United States Patent [19]
Tham et al.

[11] Patent Number: 5,857,458
[45] Date of Patent: Jan. 12, 1999

[54] AUTOMATIC BELLOWS REFILL

[75] Inventors: Robert Q. Tham, Madison; Todd Keitel, DeForest, both of Wis.

[73] Assignee: Ohmeda Inc., Liberty Corner, N.J.

[21] Appl. No.: 938,540

[22] Filed: Sep. 26, 1997

[51] Int. Cl.[6] .......................... A61M 16/10; A61M 15/00; A62B 7/04; F16K 31/26

[52] U.S. Cl. ............................... 128/203.28; 128/203.12; 128/204.28; 128/205.13; 128/205.15

[58] Field of Search .......................... 128/205.13–205.17, 128/202.22, 204.28, 205.23, 203.12, 203.24, 203.25, 205.11, 203.28

[56] References Cited

U.S. PATENT DOCUMENTS

| | | | |
|---|---|---|---|
| 3,831,595 | 8/1974 | Valenta et al. | 128/205.15 |
| 3,903,881 | 9/1975 | Weigl | 128/205.13 |
| 4,127,121 | 11/1978 | Westenskow et al. | 128/203.14 |
| 5,398,675 | 3/1995 | Henkin et al. | 128/205.15 |
| 5,662,099 | 9/1997 | Tobia et al. | 128/205.13 |
| 5,678,540 | 10/1997 | Kock et al. | 128/205.13 |

*Primary Examiner*—Kimberly L. Asher
*Attorney, Agent, or Firm*—Roger M. Rathbun

[57] ABSTRACT

A system for automatically refilling the patient breathing circuit of an anesthesia system wherein the system detects the existence of a large leak in the patient breathing system and reduces the flow of the fresh gas to the patient circuit to minimize the amount of gas that is vented to the atmosphere. As the leak is corrected, the system automatically detects that the leak has been alleviated and increases the fresh gas flow to a high flow to refill the patient breathing circuit in a rapid time. Upon refill, the system detects that the circuit and the system has been refilled and automatically reduces the fresh gas flow back to a lower level desired by the clinician to maintain the anesthesia. The fresh gas flow used to refill the patient circuit is the same composition of gases and anesthetic agent as initially set by the clinician.

12 Claims, 2 Drawing Sheets

AUTOMATIC BELLOWS REFILL

BACKGROUND

The present invention relates to anesthesia systems used to provide an anesthetic agent to a patient undergoing an operation.

In general, anesthesia systems are utilized in operating rooms and comprise various equipment necessary to anesthetize the patient and maintain the patient in that state until the operation is completed and it is possible to terminate the introduction of the anesthetic agent.

Such systems comprise various pressure regulators, flow control devices, gas mixing devices and vaporizers to vaporize a volatile liquid anesthetic and to introduce the anesthetic laden gases into the patient. The patient is connected to the system by means of a face mask or other device and which interfaces with the anesthesia system via a patient circuit that may typically have an inspiratory limb through which the gases are introduced into the patient and an expiratory limb that conveys the exhaled gases from the patient.

In one typical anesthesia system, the overall flow of gases to and from the patient may be in a generally closed circuit, commonly referred to as the circle system, that is, the patient is connected to a substantially closed volume supply of gases and rebreathes certain of those exhaled gases supplemented by fresh gas.

As the driving force to the circle breathing circuit, and, of course, to the patient, a ventilator is used and which basically breathes for the patient since the patient is under anesthesia and is unable to carry out the normal spontaneous breathing functions. The ventilator, therefore, provides a quantity of the gas containing a predetermined metered quantity of the anesthetic agent along with other gases such as nitrous oxide and, of course, a life sustaining percentage of oxygen.

That gas containing the anesthetic may typically be delivered through an intermediate mechanism such as a bellows. In such case, the driving gas from the ventilator does not contain the anesthetic agent but is used to simply power the bellows to collapse that bellows to deliver the aforementioned anesthetic containing gas from the bellows to the patient. Instead of drive gas, other driving means such as an electromechanical or mechanical means are also used.

In any of the aforedescribed systems, the anesthetic laden gas is delivered to the inspiratory limb of the circle patient breathing circuit and is introduced into the patient to provide anesthesia to that patient. That anesthetic gas to the inspiratory limb is provided by a source of gases, including fresh gas, oxygen and generally nitrous oxide, that is mixed to a predetermined mixture in a gas mixer and the mixed gases are then passed through an agent vaporizer where the anesthetic agent is introduced into those gases.

In the expiratory limb of the circle patient breathing circuit, as the patient exhales, the exhalation gases pass through the expiratory limb where they are recirculated back to the inspiratory limb where they are again inhaled by the patient. In this manner, the system is closed and which allows the optimum use of the rather expensive anesthetic agent. If the fresh gas added to the circuit exceeds the net of gases taken up by the patient or leaked from the circuit, the excess gases are popped off via a pop-off valve.

One difficulty with such system is that on occasion, there is a loss of gas within the system, that is, there may be a patient disconnect where one of the limbs to the patient becomes disconnected, or, alternatively, there may simply be a leak in the system such that the gas that normally is supplied to the patient is released to the atmosphere and the patient is not receiving the amount of gas intended by the clinician.

In such instances, it is incumbent on the clinician to recognize the problem and, commonly, the clinician continuously watches the movement of the bellows expansion and contraction as the patient is supplied with respiratory gases. If the bellows fails to expand to its full volume, that is, the expansion of the bellows is less than the clinician has been viewing, there is an indication that some gas is escaping from the system. Accordingly, the clinician may continually watch the bellows movement to see if there is a lessening of the expansion and note that indication as evidence of a leak in the patient circuit.

In such cases, when the clinician recognizes the problem, corrective action must be taken to reestablish the integrity of the breathing system and to restore the anesthesia machine back to the normal pattern of ventilating the patient. At the present, when the clinician does recognize the loss of integrity in the breathing system and makes the necessary correction to terminate the leak, the clinician then normally activates an oxygen flush that is present on all anesthesia machines and which sends a high flow of oxygen to the patient circuit. While that method may serve to reinflate the bellows and supply the needed gas to refill the overall breathing system, the composition of the gas then supplied is pure oxygen and the desired oxygen concentration to the patient that had been established to the patient by the clinician must be again reestablished to restore the original breathing conditions set by the clinician.

SUMMARY OF THE INVENTION

The anesthesia system of the present invention includes a means of detecting when there is a disconnect or large leak in the system, reduce the flow to the patient and then carry out automatic refilling of the system at a high flow when the leak has been corrected and then return the anesthesia system to the original conditions. Throughout these gas flow excursions, the gas delivery system maintains the set inspired gas composition delivered to the patient. Set inspired composition may be explicitly defined by the user or implicitly defined via expired gas composition setting as set expired agent concentration control.

In particular, the present invention relates to an anesthesia system that determines when a transitory disconnect or large leak has taken place in the breathing circuit. Upon recognition of the existence of such disconnect or large leak, the system reduces the fresh gas flow to a lower predetermined flow and retains the flow at the lower setting while the disconnect or leak is being corrected. Upon correction of the disconnect or leak, the system automatically recognizes that the fault has been corrected and increases the fresh gas flow to quickly refill the breathing circuit with the particular composition of breathing gas mixture established by the clinician.

The system thus further includes a means to determine when the breathing circuit has again been filled and automatically returns the fresh gas flow back to the original setting.

Thus, the system not only recognizes the existence of disconnections or large leaks but it carries out the refilling of the breathing circuit with a high flow of the correct gas composition and, when that breathing circuit has been refilled, the system automatically restores the previously established flows with the desired composition of breathing gas originally established.

Accordingly the clinician need not visually establish the existence of the leaks or disconnects such that the sole reliance of the clinician is eliminated and that clinician can be paying attention to other functions. Therefore, since the recognition of the leak or disconnect is automatic, the system can immediately reduce the gas flow. This minimizes gas pollution into the operating room and reduces wastage of anesthetic agent.

Also, instead of the using the oxygen flush where the concentrations are changed, the present system carries out the high flow re-establishment of the volume in the breathing circuit with gas at the proper concentrations and when the circuit has been refilled, return the flow and concentration to the original value, thus the clinician need not take any further measures to bring the system fresh gas flows and concentrations to the desired values other than to correct a disconnect or to alleviate the large leak.

As a further advantage, the time that the patient circuit takes to refill is also minimized since the system senses the correction of the circuit fault and takes the corrective action to restore the gas to the breathing circuit without user intervention, that is, the refilling operation is automatic and does not require any user action to refill the circuit. Increasing the gas flow also speeds up the recovery time of the gas volume.

Other objects, features and advantages of the present invention will be more apparent from the detailed description of the preferred embodiments set forth below, taken in conjunction with the accompanying drawings.

DETAILED DESCRIPTION OF THE INVENTION

Figure 1:
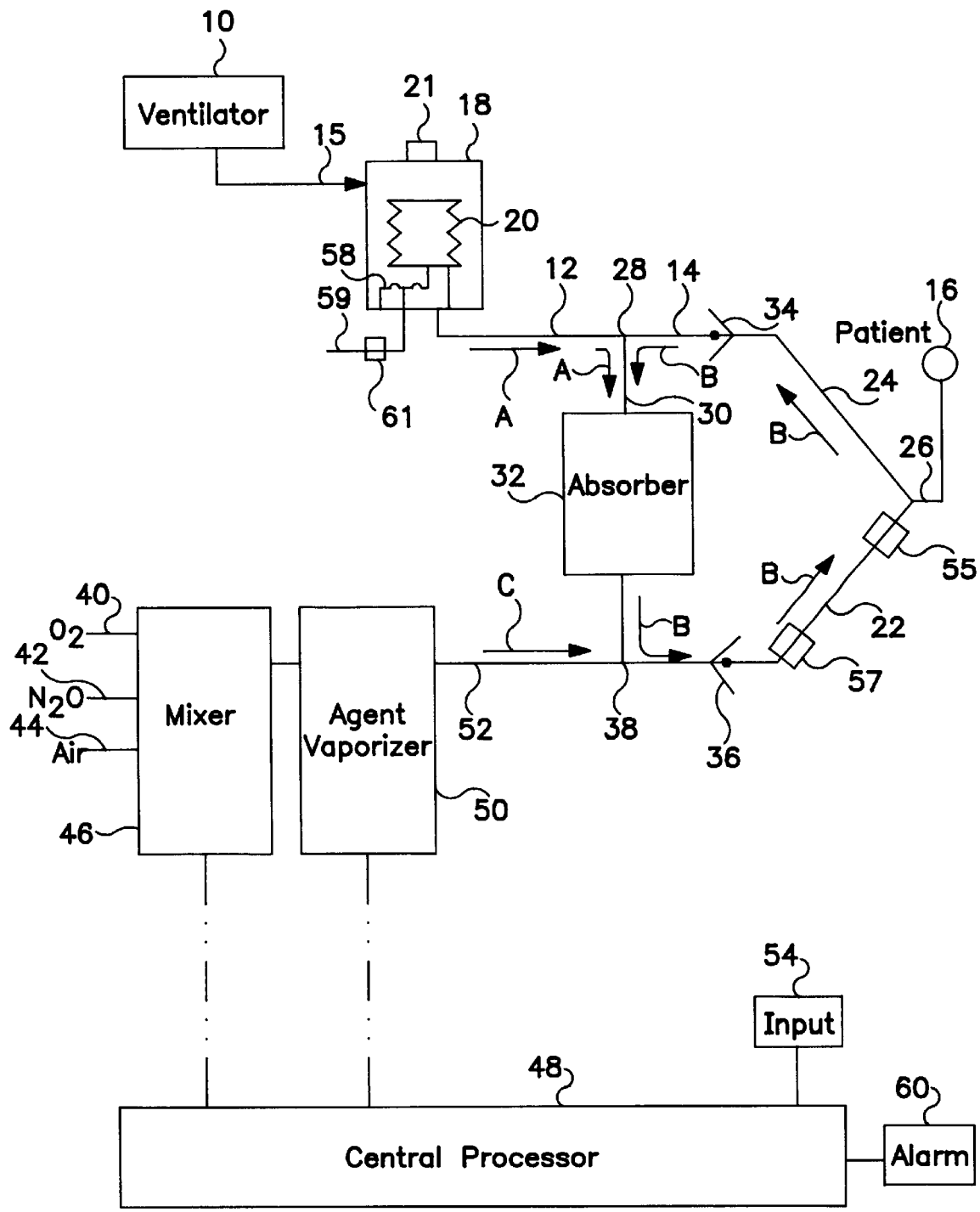
FIG. 1 is a block diagram of the components of an anesthesia system used to carry out the present invention.

Referring now to FIG. 1, there is shown a block diagram of an anesthesia system adapted to carry out the subject invention. As shown, a ventilator 10 is provided and which may be of the type shown and described in U.S. Pat. No. 5,315,989 assigned to the present applicant and the disclosure of which is incorporated herein by reference. The present system can also be applied to the anesthesia ventilator system disclosed in U.S. Pat. No. 5,094,235 of Westenskow. The ventilator of the aforementioned U.S. Pat. No. 5,315,989 has an inhalation cycle and an exhalation cycle controlled by a central processing unit.

The ventilator 10 provides gas to the patient during the inhalation cycle via a conduit 12 to the patient breathing circuit 14 where it is delivered to the patient 16. The ventilator 10 typically includes a bellows container 18 and air or other powering gas is supplied to the bellows container 18 via conduit 15, exterior of the bellows 20 and which then collapses the bellows 20 to force gas within the bellows 20 to the patient 16. A means of determining the amount of inflation of the bellows 20 is also included and which indicates the maximum volume of gas that is contained in the bellows 20 at the end of its expansion. That means may be a top bellow sensor 21 located at the top of the bellows container 18 and which senses when the top of the bellows 20 approaches the top of the bellows container 18.

Alternatively, a bellows position sensor 23 can be used as will be explained and which may be positioned along the side of the bellows container 18 and which can detect the position of the top of the bellows 20 in any one of many positions within the bellows container 18. An example of such a bellows position sensor 23 is shown and described in the aforementioned Westenskow U.S. Pat. No. 5,094,235.

As also noted in the aforementioned U.S. Pat. No. 5,315,989, the patient breathing circuit 14 itself conventionally includes an inspiratory limb 22 and an expiratory limb 24 and the patient 16 is connected to a wye connection 26 located intermediate the inspiratory and the expiratory limbs 22,24. The means of connection to the patient 16 may be an endotracheal tube, face mask or other interface between the patient 16 and the patient breathing circuit 14.

In conventional operation, gas is delivered to the patient 16 by means of a powering gas from ventilator 10 that collapses the bellows 20 to drive the gas into conduit 12 and then into the tee 28 where the gas enters a conduit 30 and passes through an absorber 32. After passing through the absorber 32, the gas enters the inspiratory limb 22 of the patient breathing circuit 14 to be administered to the patient 16. As the patient exhales, that exhalation, now laden with $CO_2$, passes through the expiratory limb 24 where it again passes through the tee 28 and continues to the absorber 32 where the $CO_2$ is eliminated by a $CO_2$ absorbing material, such as sodalime.

A pair of check valves 34 and 36 are positioned in the patient breathing circuit 14 in the expiratory and inspiratory limbs 24 and 22, respectively, to maintain the flow of gas in the proper direction around the circle patient breathing circuit 14.

A flow of fresh gas is also introduced into the patient breathing circuit 14 and, as shown, is added at a tee 38 and thus into the inspiratory limb 22 of the patient breathing circuit 14. That flow of fresh gas is provided from a source of gas, typically oxygen and nitrous oxide to aid in anesthetizing the patient. As shown in the Figure, there is a supply of oxygen 40, nitrous oxide 42 and air 44 and such supplies may be through a central piping system of a hospital or may be through the use of individual cylinders of such gases.

In any event, the gases are mixed in a gas mixer 46 in the proportion desired by the user. The actual control of the proportions and the flow through the gas mixer 46 is, in the preferred embodiment, controlled by a central processing unit (CPU) 48 as will be described. The mixed gas from the gas mixer 46 then passes through an agent vaporizer 50 where liquid anesthetic agent is vaporized and added to the stream of gas such that anesthetic laden gas continues into a conduit 52 and enters the patient breathing circuit 14 at the tee 38.

Again, in the preferred embodiment, the control of the agent vaporizer 50 is by means of the CPU 48 and which determines the percentage concentration of anesthetic agent that is in the gas that enters the patient breathing circuit 14 and thus that is supplied to the patient 16 to induce and maintain anesthesia.

The CPU 48 is, in turn, controlled by an input device 54 provided so that the clinician can input the data needed to determine the various parameters to provide the fresh gas flow and anesthetic concentration desired to anesthetize the patient. The input to the CPU 48 may be the flow of fresh gas to the patient as well as the concentrations of the various gases mixed in the gas mixer 46 and the concentration of anesthetic to be added to the mixed fresh gas by the agent vaporizer 50.

The overall flow scheme of the present conventional system is therefore such that the gas in the bellows 20 is forced by the ventilator 10 into conduit 12 in accordance with the arrows A during the inhalation cycle of the patient 16. The gas thus passes through the tee 28 and through absorber 32 where it further passes through tee 38 and into the inspiratory limb 22 of the patient breathing circuit 14. At tee 38, fresh gas containing a predetermined concentration of an anesthetic agent is joined with the gas from the bellows 20 and proceeds with the gases already circulating in patient breathing circuit 14 and administered to the patient 16.

When the patient exhales, the exhaled gas passes through the expiratory limb 24 of the patient breathing circuit 14 through tee 28 and continues through the conduit 12 and into the bellows 20. At the same time, fresh gas that continuously flows into the circuit 14 from conduit 52 is also directed towards the bellows 20 after passing through the patient breathing circuit 14. When the bellows 20 reaches the end of its travel, any excess gas is popped off from the bellows 20 via pop-off valve 58 and exits the system via conduit 59 and typically into a gas scavenging system, not shown.

A flow sensor 61 is located in the flow of gas from the pop-off valve 58 and senses the flow from that pop-off valve. As such, the flow exits the pop-off valve 58 due to the pressure differential between the interior of the bellows 20 and the ambient pressure and is an indication of the position of the bellows 20 and, as explained, an indication of the maximum amount of gas that is introduced into the bellows 20. That is, the gas escapes the pop-off valve 58 due to the existence of excess gas in the bellows 20 when the bellows 20 reaches its uppermost position and the continued flow of gas into the bellows 20 results in an increase in pressure, opening the pop-off valve 58 releasing the gas to atmosphere or to a scavenging system. Thus, the existence of a flow of gas out of the pop-off valve 58 is an indication the bellows 20 has reached its uppermost position within the bellows container 18. As can thus be seen, a flow out of the pop-off valve 58 confirms that the bellows has reached its uppermost position. An alternate sensor could be employed to confirm that the bellows 20 has reached that top position including a sensor that merely detects that the pop-off valve 58 has opened to allow that excess gas to escape.

During the inspiratory phase, the bellows 20 is driven downwardly by the ventilator 10. The unidirectional check valves 34 and 36 direct the gas from the bellows 20 to conduit 12 and through the absorber 32 where the gas is scrubbed of $CO_2$. Also directed is the fresh gas from conduit 52 towards the patient 16 via inspiratory limb 22 of breathing circuit 14.

As can be seen, therefore, the anesthesia system is basically a circle system where the gas continues to pass in a circle as shown by the arrows B with the addition of fresh gas and the anesthetic agent added to that gas in the direction of Arrow C as the gas passes around the circle.

As further components of the overall anesthesia system, a pressure sensor 55 is present in the inspiratory limb 22 and is indicative of the pressure in the patient breathing circuit or airway, that is $P_{AW}$ and a flow sensor 57 is also present in the same inspiratory limb 22 and which detects the flow $Q_{AW}$ of gas in the patient circuit or airway. The signals representative of the pressure monitored by the pressure sensor 55 and the flow monitored by flow sensor 57 are provided to CPU 48 for purposes that will be hereinafter explained.

Figure 2:
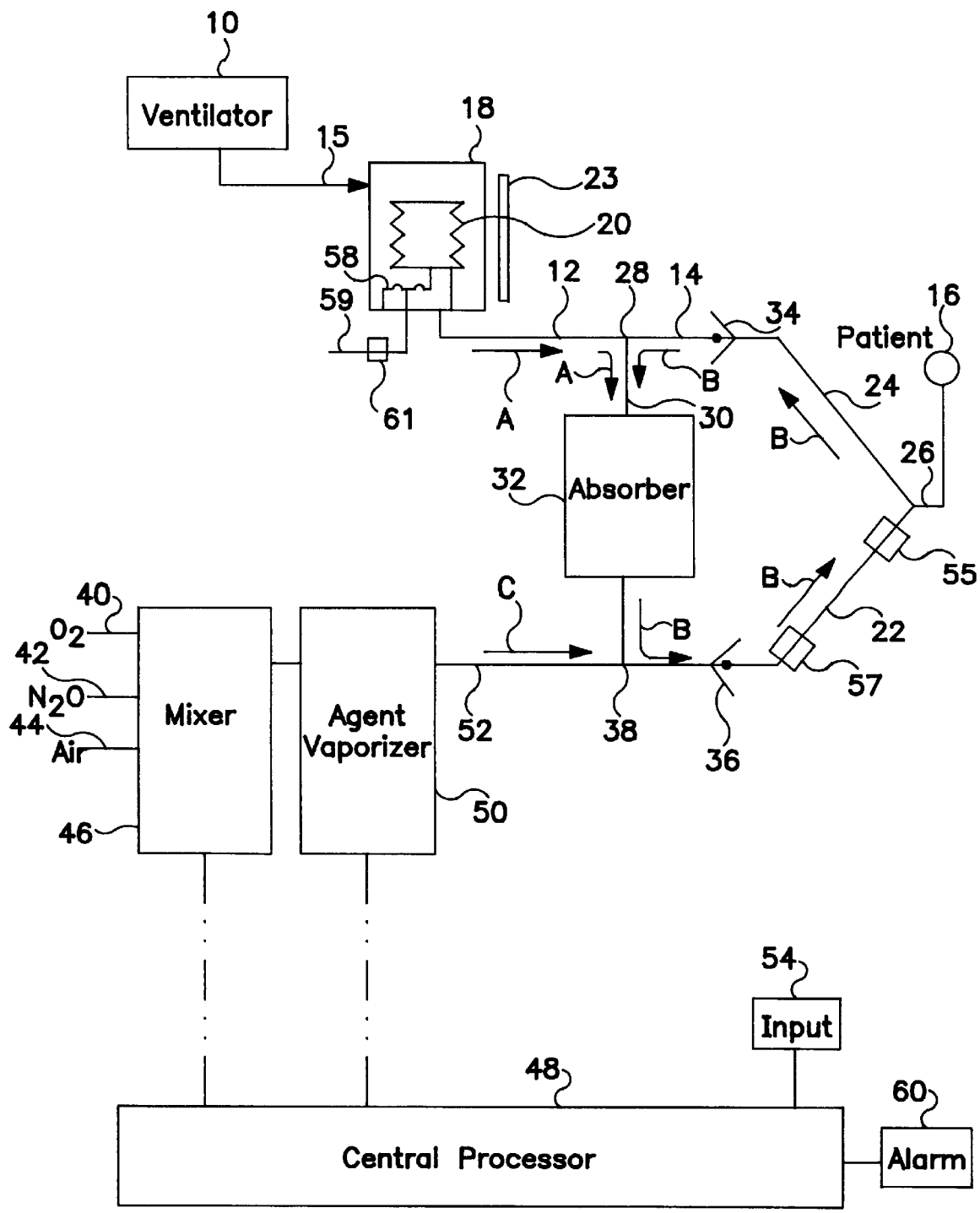
FIG. 2 is a block diagram of an alternate embodiment of the anesthesia system of FIG. 1.

In accordance with the present invention, therefore, the system determines when there is a leak in the breathing circuit or a loss of integrity in the system. As described, there are various embodiments that can detect the existence of a leak, one of which is to utilize the top bellows sensor 21 that will determine whenever the bellows 20 does not reach the top of the bellows container 18, thus indicating that there is a loss of gas somewhere in the closed anesthesia system. Alternatively, the bellows position sensor 23 (See FIG. 2) may be used to continuously monitor the uppermost position reached by the bellows 20 during normal respiration of the patient 16 and that bellows position sensor 23 of FIG. 2 can be activated if the bellows 20 does not return to the same maximum vertical height within the bellows container 18. As a further indication of a leak in the patient circuit 14, the flow sensor 61 on the pop-off valve 58 can be used. Whenever there is no flow from the pop-off valve 58, it is an indication that the bellows 20 has not reached its uppermost position within the bellows container 18 and thus is an indication that gas is leaking from the overall breathing circuit. As a further alternative, a sensor 61 may be used at or downstream of the pop-off valve 58 that merely indicates that the pop-off valve 58 had not opened at the end of the expiration cycle of the ventilator, again, indicating that the bellows 20 did not reach its uppermost position within the bellows container 18. If the position of the bellows is not explicitly measured, it is preferable that the indication of a disconnect or large leak be confirmed, for example, by determining that the bellows did not reach the top some time. Confirmation may also be drawn from the ventilator itself where it is unable to deliver the set tidal breath or minute ventilation.

In any event, the detection of a loss of integrity in the patient circuit 14 is communicated to the CPU 48, by one of the various sensors previously described and the CPU 48 thus immediately reduces the fresh gas flow from the mixer 46 to a lower level. If not already at the low level of flow, the CPU 48 instructs the mixer to reduce the flow to a minimum set for rate i.e. 1 liter per minute, or, alternatively, in to a minimum fresh gas flow preset by the clinician. It is important to note, however, that the overall concentrations of the various gases within the flow of fresh gas are not altered, the CPU 48 merely affects the flow of the fresh gas and its composition remains the same as already established by the clinician. By immediately lowering the flow of the fresh gas to the patient circuit, the system minimizes the amount of the gas that is leaked to the atmosphere surrounding the operating room environment so that the potentially hazardous gases are minimized from being inhaled by the clinicians that are carrying out the particular operation.

As a part of the system, there may be some alarm or alert given to the clinician advising of the leak in the patient breathing circuit so that immediate action can be taken to correct that leak.

When the leak has been corrected by the clinician or the attending personnel, the system recognizes that the leak has been corrected. When the leak is corrected, the fresh gas will begin to refill the patient circuit with the breathing gas. That refilling process can be recognized by the present system and appropriate further steps taken. The refilling can be detected by the use of the bellows position sensor 21 which will detect that the bellows 20 will begin to refill. The system, to be sure, may note a few successive breaths where the bellows 20 increases its vertical movement with each breath to assure the system that the leak has, indeed, been corrected and the integrity of the system restored. Alternatively, the correction of the leak may be determined by the pressure sensor 55 that will note a steady breath-to-breath increase in pressure in the system as bellows 20 becomes refilled. As a still further alternative, the tidal volume will continuously increase and that volume may be detected by the flow sensor 57 and the volume obtained by integrating the detected flow along with the time of the inspiratory cycle. In any of these methods, the system will recognize that the leak has been corrected and the volume in the patient circuit is gradually being refilled.

At this point, when the system has confirmed that the patient circuit 14 is refilling, thereby determining that the leak has been corrected, the CPU 48 immediately increases the fresh gas flow to a large value, i.e. 15 liters per minute to quickly refill the patient breathing circuit. Again, it is noted that the increased flow of fresh gas is filled with gas at the desired composition that has been previously established by the clinician, the only change is that the CPU 48 has increased the flow from the gas mixer 46 to the higher flow so that the circuit may be refilled as quickly as possible.

The system of the present invention then detects the refilling and determines when the system has been sufficiently refilled with fresh gas. That detection may be carried out by again detecting the flow of excess gas out of the pop-off valve 58 indicating that the bellows 20 is again reaching its uppermost point within the bellows container 18 or, again, by simply detecting that the pop-off valve 58 has indeed opened. Alternatively, the detection of the circuit refill may be by means such as the bellows position detector 23 that will note the bellows 20 is again reaching its maximum vertical extension, or by the top bellows sensor 21 that again detects that the bellows is returning to its maximum vertical position. As a precaution, the CPU 48 also notes the amount of fresh gas that is provided to the system after the system has sensed that the leak has been corrected such as the detection of the delivery of 2.5 liters of fresh gas into the patient breathing circuit. If no sensor, of any of the above, has confirmed that the system has been refilled after delivery of that volume at the high flow, the system returns the flow back to the minimum flow previously established upon the determination of a lack of integrity of the patient breathing circuit and assumes that the leak or disconnect has not really been corrected. The low flow is continued until there is again some indication through the sensors that the leak has been alleviated.

As a last step, when the appropriate sensor of the last step determines that the patient circuit has been refilled, the CPU 48 lowers the flow back to the originally set flow established by the clinician and the ventilation of the patient is returned to the conditions that existed prior to the occurrence of a leak. That reduced flow may be at lowest flow that satisfies the metabolic $O_2$ and agent usage demand in accordance with the system disclosed in copending U.S. patent application Ser. No. 730,508, filed Nov. 11, 1996 and entitled Method and Apparatus For Controlling an Anesthesia Delivery System and owned by the present assignee.

Accordingly to summarize the system of the present invention, the system detects the occurrence of a large leak or disconnect in a patient breathing circuit used with a patient undergoing anesthesia. At the detection of that large leak or disconnect, the system reduces the fresh gas flow, or alternatively, assures that fresh gas flow is at a low flow that is predetermined or is reduced to a set minimum. The system continues to monitor the patient breathing circuit and detects when the leak or disconnect has been corrected by the clinician and immediately increases the fresh gas flow to the patient breathing circuit at the same gas concentrations as were being provided to the patient to quickly refill the patient circuit. The system further detects when the circuit has been refilled and when that occurrence has been detected, the system returns the fresh gas flow to a lower level, such as a minimum gas flow or to the desired gas flow setting originally being provided to the patient.

While the present invention has been set forth in terms of a specific embodiment, it will be understood that the anesthesia system herein disclosed may be modified or altered by the those skilled in the art to other configurations. Accordingly, the invention is to be broadly construed and limited only by the scope and spirit of the claims appended hereto.

We claim:

1. An anesthesia system having a ventilator having an inspiratory cycle for providing a breathing gas to a patient through a patient breathing circuit and an expiratory cycle where the patient exhales, a gas mixer adapted to supply fresh gas to said patient breathing circuit at a set inspired composition and at a first flow rate, said system comprising means to sense a leak in the patient breathing circuit, means to reduce the flow rate of said gas from said gas mixer upon detection of a leak to a second flow rate substantially lower than said first flow rate, means to sense when a leak has been corrected and said patient breathing circuit is being refilled, said system further including means to increase the flow of said fresh gas to a third flow rate substantially higher than said first flow rate upon sensing the refilling of said patient breathing circuit, and a sensor to detect when said patient breathing circuit has been refilled to reduce the flow of fresh gas back to said first flow rate.

2. An anesthesia system as defined in claim 1 wherein said second flow rate is a minimum flow rate preestablished by the user.

3. An anesthesia system as defined in claim 1 wherein said anesthesia system further comprises a bellows that collapses to force gas to the patient during said inspiratory cycle and expands to a maximum expansion during the expiratory cycle, and said means to detect a leak comprises a sensor monitoring the position of said bellows.

4. An anesthesia system as defined in claim 3 wherein said sensor to determine when said patient breathing circuit has been refilled comprises a sensor monitoring the position of said bellows.

5. An anesthesia system as defined in claim 3 wherein said means to sense when a leak has been corrected comprises a sensor monitoring the position of said bellows.

6. An anesthesia system having a ventilator having an inspiratory cycle for providing a breathing gas to a patient through a patient breathing circuit and an expiratory cycle where the patient exhales, a gas mixer adapted to supply fresh gas to said patent circuit at a set inspired composition and at a first flow rate, said system comprising means to sense a leak in the patient breathing circuit, means to reduce the flow rate of said gas from said gas mixer upon detection of a leak to a second lower flow rate, means to sense when said patient breathing circuit is refilling, and means to increase the flow to a flow substantially higher than said first flow rate of fresh gas to said patient breathing circuit at said set inspired composition to rapidly refill said patient breathing circuit.

7. An anesthesia system as defined in claim 6 wherein said means to sense when said patient breathing circuit is refilling comprises a pressure sensor in said patient circuit to detect an increase of pressure in said patient breathing circuit.

8. An anesthesia system as defined in claim 6 wherein said means to sense when said patient breathing circuit is refilling comprises a flow sensor in said patient circuit to detect an increase of volume over a predetermined time in said patient breathing circuit.

9. An anesthesia system having a ventilator having an inspiratory cycle for providing a breathing gas to a patient through a breathing circuit and an expiratory cycle where the patient exhales, said system having a bellows that collapses to force gas to the patient during said inspiratory cycle and expands to a maximum expansion during the expiratory cycle, said bellows further comprising a pressure actuated valve communicating with the interior of said bellows and said pressure actuated valve is adapted to open to vent gas from said bellows when a predetermined differential pressure is attained across said valve, said system including means to detect a leak in said patient circuit by monitoring the amount of said maximum expansion of said bellows, said means comprising a flow detector adapted to monitor flow from said pressure actuated valve.

10. An anesthesia system having a ventilator having an inspiratory cycle for providing a breathing gas to a patient through a breathing circuit and an expiratory cycle where the patient exhales, said system having a bellows that collapses to force gas to the patient during said inspiratory cycle and expands to a maximum expansion during the expiratory cycle, said bellows further comprising a pressure actuated valve communicating with the interior of said bellows and said pressure actuated valve is adapted to open to vent gas from said bellows when a predetermined differential pressure is attained across said valve, said system including means to detect a leak in said patient circuit by monitoring the amount of said maximum expansion of said bellows, said means comprising a sensor to determine when said pressure actuated valve has opened.

11. An anesthesia system having a ventilator having an inspiratory cycle for providing a breathing gas to a patient through a breathing circuit and an expiratory cycle where the patient exhales, said system having a bellows that collapses to force gas to the patient during said inspiratory cycle and expands to a maximum expansion during the expiratory cycle, said bellows further comprising a pressure actuated valve communicating with the interior of said bellows and said pressure actuated valve is adapted to open to vent gas from said bellows when a predetermined differential pressure is attained across said valve, said system including means to detect a leak in said patient circuit by monitoring the amount of said maximum expansion of said bellows, and means to detect the correction of a leak by monitoring the expansion of said bellows, said means to detect the correction of a leak comprising a sensor to determine when said valve has opened.

12. An anesthesia system having a ventilator having an inspiratory cycle for providing a breathing gas to a patient through a breathing circuit and an expiratory cycle where the patient exhales, said system having a bellows that collapses to force gas to the patient during said inspiratory cycle and expands to a maximum expansion during the expiratory cycle, said bellows further comprising a pressure actuated valve communicating with the interior of said bellows and said pressure actuated valve is adapted to open to vent gas from said bellows when a predetermined differential pressure is attained across said valve, said system including means to detect a leak in said patient circuit by monitoring the amount of said maximum expansion of said bellows, and means to detect the correction of a leak by monitoring the expansion of said bellows, said means to detect the correction of a leak comprising a flow detector adapted to monitor flow from said pressure actuated valve.

* * * * *